(12) United States Patent
Srivatsa et al.

(10) Patent No.: US 8,465,441 B2
(45) Date of Patent: Jun. 18, 2013

(54) CANNULA WITH INTRODUCER, NEEDLE PROTECTING GUARD AND BLOOD COLLECTING SYSTEM

(76) Inventors: Kadiyali Madhava Srivatsa, Woking (GB); Martina Benzing, Woking (GB)

( * ) Notice: Subject to any disclaimer, the term of this patent is extended or adjusted under 35 U.S.C. 154(b) by 0 days.

(21) Appl. No.: 13/227,265

(22) Filed: Sep. 7, 2011

(65) Prior Publication Data

US 2012/0004574 A1 Jan. 5, 2012

Related U.S. Application Data

(63) Continuation of application No. 11/911,810, filed as application No. PCT/GB2006/001408 on Apr. 19, 2006, now abandoned.

(30) Foreign Application Priority Data

Apr. 19, 2005 (GB) .................................. 0507969.4
Jul. 19, 2005 (GB) .................................. 0514766.5

(51) Int. Cl.
*A61B 5/00* (2006.01)

(52) U.S. Cl.
USPC .......................................... 600/576; 604/198

(58) Field of Classification Search
USPC ............................ 600/576; 604/192, 197, 198
See application file for complete search history.

(56) References Cited

U.S. PATENT DOCUMENTS

| 4,955,866 A | | 9/1990 | Corey | |
|---|---|---|---|---|
| 5,120,311 A | * | 6/1992 | Sagstetter et al. | ............ 604/110 |
| 5,336,199 A | * | 8/1994 | Castillo et al. | ................ 604/198 |
| 5,411,486 A | | 5/1995 | Zadini | |
| 5,466,223 A | * | 11/1995 | Bressler et al. | ................ 604/110 |
| 5,487,733 A | | 1/1996 | Caizza | |
| 5,569,210 A | | 10/1996 | Moen | |
| 5,951,529 A | | 9/1999 | Utterberg | |
| 6,001,080 A | | 12/1999 | Kuracina | |
| 6,004,278 A | | 12/1999 | Botich | |
| 6,056,726 A | * | 5/2000 | Isaacson | .................. 604/164.01 |
| 6,159,185 A | | 12/2000 | Tanihata | |
| 6,475,191 B2 | * | 11/2002 | Tamura et al. | ........... 604/164.08 |
| 6,716,199 B2 | * | 4/2004 | DeHarde et al. | .............. 604/263 |
| 2006/0074349 A1 | | 4/2006 | Fan | |
| 2006/0189934 A1 | * | 8/2006 | Kuracina et al. | .............. 604/110 |

FOREIGN PATENT DOCUMENTS

EP 01/142603 10/2001

OTHER PUBLICATIONS

International Search Report from PCT/GB2006/01408 completed Jul. 6, 2006.
U.S. Appl. No. 11/911,810, Nov. 23, 2010, Office Action.
U.S. Appl. No. 11/911,810, Mar. 7, 2011, Office Action.

* cited by examiner

*Primary Examiner* — Max Hindenburg
(74) *Attorney, Agent, or Firm* — Workman Nydegger

(57) ABSTRACT

A cannula introducing device comprises an elongate body (10) having a needle (12) projecting from a front end, an operating element (24) for displacement longitudinally of the body (10), a plunger (16) disposed at the front end of the body (10), and a coupling means (18), such as a flexible wire, coupling the operating element (24) and the plunger (16), arranged so that retraction of the operating element (24) serves to advance the plunger (16) over the needle (12) and so advance the cannula (30) which is disposed over the needle.

20 Claims, 4 Drawing Sheets

CANNULA WITH INTRODUCER, NEEDLE PROTECTING GUARD AND BLOOD COLLECTING SYSTEM

This application is a continuation of U.S. patent application Ser. No. 11/911,810, filed May 20, 2008 now abandoned, which is a national stage entry of PCT Application No. PCT/GB2006/01408, filed Apr. 19, 2006, which claims priority to Great Britain application number 0507969.4, filed Apr. 19, 2005, and Great Britain application number 0514766.5, filed Jul. 19, 2005, all of which are incorporated herein in their entirety.

The present invention relates to medical devices including devices for introducing a cannula into a patient's blood vessel and for collecting a sample of blood or other bodily fluid.

Intravenous cannulation is an important procedure particularly in the management of acutely ill patients. The procedure is carried out using a needle inserted through the cannula, with the tip of the needle projecting from the forward end of the cannula, then inserting the tip of the needle into an artery or vein, and finally advancing the cannula over the tip of the needle to introduce its forward end into the blood vessel, then withdrawing the needle. This procedure requires very fine hand control and considerable practise on the part of the doctor carrying it out. Moreover, cannulation is occasionally complicated and in any event takes time and places the patient under considerable stress.

Cannula introducing devices have hitherto been arranged for user to move the cannula forwardly, over the tip of the needle, using the index finger. This forward movement of the cannula must be performed swiftly once the tip of the needle has entered the lumen of the blood vessel: any slight movement of the tip of the needle in the blood vessel lumen may result in puncture and failed cannulation; any withdrawal of the tip of the needle, prior to cannula placement in the lumen, will also result in failure. U.S. Pat. No. 5,338,306 is directed to a cannula introducing device which uses either a mechanical spring or a compressed air spring, released by the user once the tip of the needle has been inserted into the blood vessel, to advance the cannula over the needle and into the blood vessel.

I have now devised a cannula introducing device which is reliable to use and does not include any form of spring, at least for initial introduction of the cannula into the blood vessel.

In accordance with the present invention, there is provided a cannula introducing device which comprises an elongate body having a needle projecting from one end thereof, an operating element mounted to said body for displacement longitudinally thereof, a plunger disposed at said one end of the body, and means coupling said operating element and said plunger and arranged so that displacement of said operating element away from said one end of the body causes displacement of said coupling means to advance said plunger along said needle.

In use, a cannula is slipped over the needle to abut the plunger of the device, with the tip of the needle projecting from the forward end of the cannula. Then the user grips the body of the device and brings the assembly up to the patient to insert the tip of the needle into a blood vessel. The user then retracts the operating element of the device, typically using the index finger, to advance the plunger and so advance the forward end of the cannula over the tip of the needle and into the blood vessel. The device can then be withdrawn, to withdraw the needle, firstly from the blood vessel and then from the cannula, leaving the cannula inserted into the blood vessel: as the device is withdrawn, the retracting movement of the manual operating element may be continued, to continue the advancement of the plunger: preferably the arrangement is such that the plunger will advance far enough to cover the tip of the needle, and so prevent any possible needle stick injuries.

In an alternative embodiment, the plunger is arranged to be advanced an initial distance by the retracting displacement of the operating element (preferably sufficient to advance the tip of the cannula over the tip of the needle and provide initial introduction of the tip of the cannula into the blood vessel), and the device further comprises a spring (either a mechanical spring or a gas spring) which then serves to advance the plunger through a further distance: preferably the plunger, in its fully-advanced position, covers the tip of the needle, to prevent any possible needle-stick injuries.

Preferably the device includes means for preventing the plunger being retracted after it has been advanced: this prevents the device being re-used, with the risk of spreading infection. Preferably, in order to prevent the plunger being retracted, the coupling means is provided with a series of ratchet serrations which co-operate with a tooth or projection with which the body of the device is provided.

The coupling means may comprise an elongate flexible element extending along a guideway of said body, between the operating element and the cannula-advancing plunger, the elongate flexible element being displaced longitudinally of itself as the operating element is retracted. This elongate flexible element maybe arranged to push the plunger forwardly, or it may be arranged to pull on a rearward extension of the plunger to pull the plunger forwardly.

Preferably the guideway comprises a groove or channel formed in the body of the device, the operating element being engaged into and retained by this groove or channel for sliding movement along it. Preferably the operating element comprises a member which projects outwardly from the guide groove or channel, for the user to engage manually, typically with the index finger.

In one embodiment the guideway further comprises a passage having a first portion which extends from the rear end of the guide groove or channel and curves round to a second portion which extends forwardly to the front end of the body. In another embodiment, the guideway has a first portion which extends from the forward end of the guide groove or channel and curves round to a second portion which extends rearwardly of the body. Preferably the latter, second portion of the passage is disposed in or adjacent a surface of the body remote from or opposite the surface in which the guide groove or channel is formed.

The elongate element which interconnects the operating element and the plunger may comprise a wire, preferably of a flat cross-sectional profile.

Preferably the body of the device is arranged to receive a blood-collecting container for receiving blood which flows along the needle of the device when its tip is inserted into a blood vessel. Preferably the device includes an internal chamber to receive blood through the needle, this chamber being provided with a plunger which is retracted, upon retraction of the operating element of the device, or of a secondary operating element associated therewith, for a piercing needle of this plunger to pierce a membrane closing the end of the blood-collecting container: preferably the blood-collecting container is pre-evacuated or otherwise arranged to provide a vacuum so that the blood is drawn into the container.

Also in accordance with the present invention, there is provided a device for collecting a sample of blood or other fluid, the device comprising an elongate body having a needle projecting from one end thereof, the body having an interior compartment for receiving a fluid-collecting container and having a plunger disposed therein, the device further comprising an operating element arranged for displacement longitudinally of said body away from said one end thereof, in order to displace said plunger and for a piercing needle provided on said plunger to pierce a membrane which closes said container.

The device may be arranged to create a vacuum in the fluid-collecting container, as the container is inserted longitudinally into the device body. For example, the interior compartment of the device body may be provided with an elongate pusher element directed to pierce the membrane of the container as the latter is inserted, and then bear on a piston provided within the container, such that as the container is inserted, the pusher displaces the piston along the container to create a vacuum in the space between the piston and the membrane. Further in accordance with the present invention, there is provided a container for collecting a sample of blood or other fluid, the container being of tubular form and having one end closed by a piercable membrane and having an internal piston positioned adjacent said membrane.

Embodiments of the present invention will now be described by way of examples only and with reference to the accompanying drawings, in which.

Figure 1:
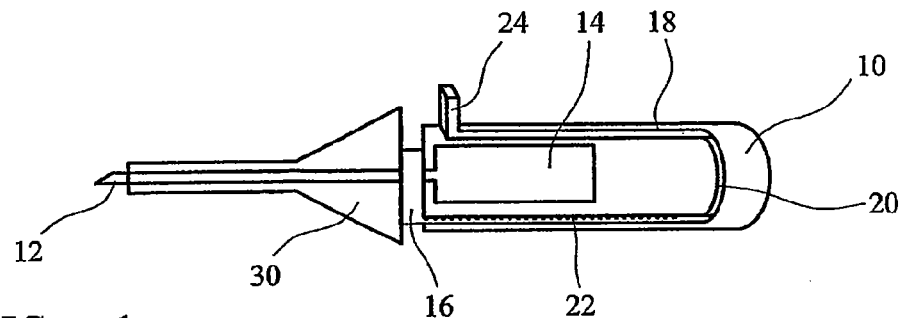
FIG. 1 is a side view, partly in section, of a first embodiment of cannula introducing device in accordance with this invention, shown with a cannula disposed over the needle of the device and the assembly in an initial condition ready for use.
Figure 2:
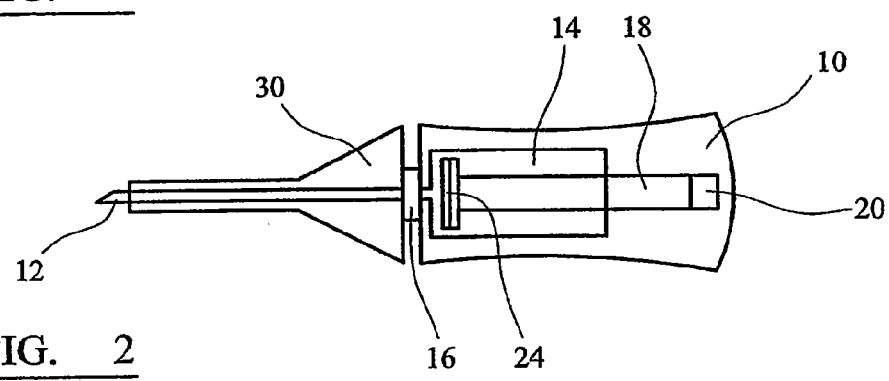
FIG. 2 is a top plan view of the assembly shown in FIG. 1.

Referring to FIGS. 1 and 2 of the drawings, there is shown a cannula introducing device which comprises an elongate body 10 having a hollow needle 12 projecting from a forward end thereof, the interior of the needle communicating with a blood collecting chamber 14 within the body 10. The device further comprises a plunger 16, in the form of a flat plate, initially disposed against the front end of the body 10 and having a central aperture through which the needle 12 extends. A guide groove 18 is formed along an upper side of the body 10, the groove 18 extending from a point adjacent the front end of the body 10 to a point adjacent the rear end of the body 10, where it joins a passage 20 which extends though the body 10, firstly curving across the body 10 towards its lower side and then extending longitudinally of the body 10 to its front end. A guide wire 22 extends along the groove 18 and then along the passage 20, the guide wire 22 having one end attached to an operating knob 24 and its other end attached to the plunger 16: the operating knob 24 is engaged with the groove 18 so as to be slidable along this groove, whilst being retained by it; also, the operating knob 24 projects outwardly from the groove 18, to enable the user to engage it and slide it rearwardly along the groove. The guide wire 22 is resiliently flexible so that, as the operating knob 24 is slid rearwardly of the body 10, the wire will displace along the passage 20 and so advance the plunger 16 along the needle 12.

In use, the plunger 16 is initially in the retracted position shown in FIGS. 1 and 2, in contact with the front end of the body 10. A cannula 30 is then slipped over the needle 12, for its rear end to abut the plunger 16 and the tip of the needle to project from the forward end of the cannula. It will be noted that the cannula 30 comprises a tubular stem having an enlarged, conical rear end. The user grips the body 10 in one hand and brings the assembly up to the patient to insert the needle 12 carefully into a blood vessel: then the user engages the operating knob 24 with his or her index finger, and moves this rearwardly along its guide groove 18, so displacing the guide wire 22 lengthwise of itself and along the groove 18 and passage 20, to advance the plunger 16; the plunger 16 accordingly pushes the cannula forwardly along the needle, so that the forward end of the cannula passes over the tip of the needle and into the blood vessel.

Figure 3:
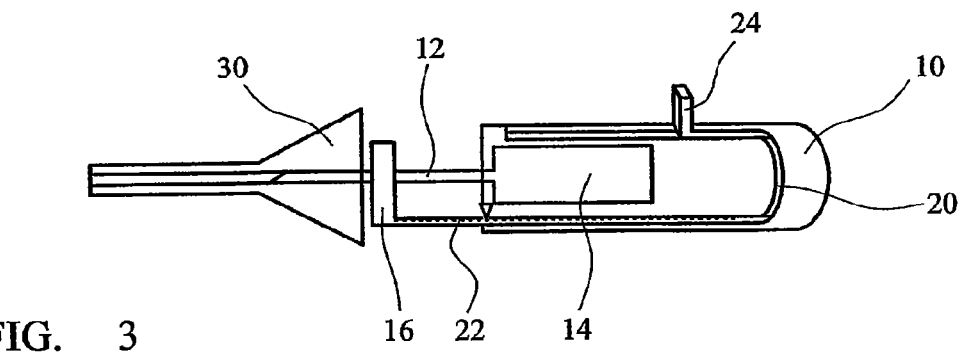
FIG. 3 is a side view of the assembly, corresponding to FIG. 1, showing the cannula once advanced over the tip of the needle and the device partly withdrawn.
Figure 4:
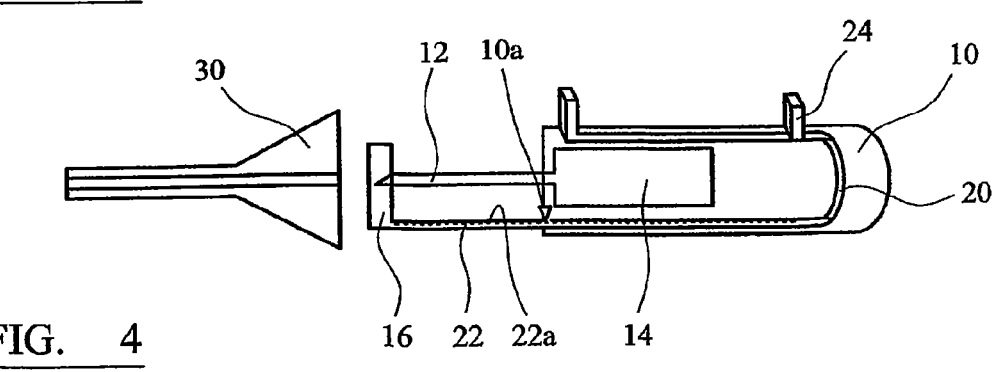
FIG. 4 is a similar view of the assembly, once the device has been completely withdrawn from the cannula and the plunger of the device fully advanced to cover the tip of the needle.

Once the cannula is in position, and referring to FIGS. 3 and 4 of the drawings, the body 10 can be withdrawn to withdraw the needle, firstly from the blood vessel and finally from the cannula: throughout this movement, the rearward displacement of the operating knob 24 is continued, so that the plunger 16 continues to advance and, finally, covers the sharp end of the needle 12. Accordingly, the tip of the needle is covered and possible needle stick injuries are prevented.

The guide wire 22 is formed with a series of ratchet serrations 22a which co-operate with a tooth 10a formed on the body 10 of the device, at or adjacent its front end: this prevents the device being re-used, with the risk of spreading infection.

It will be appreciated that the device which has been described is of relatively simple construction yet easy to use, whilst minimising the risk of movement of the needle tip as the cannula is advanced over the needle and into the blood vessel. The device avoids the use of springs and, moreover, provides for the sharp tip of the needle to become covered at the end of the cannulation procedure.

Figure 5:
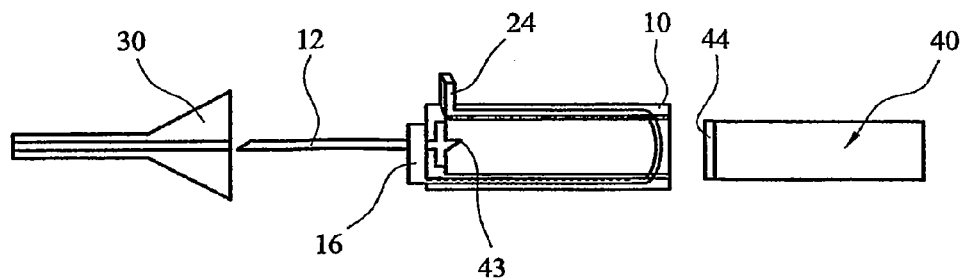
FIG. 5 is a view, similar to FIG. 1, of a second embodiment of device in accordance with the present invention.
Figure 6:
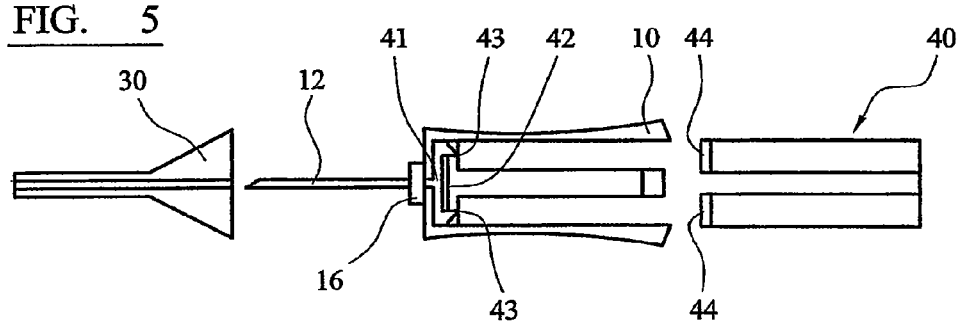
FIG. 6 is a view, similar to FIG. 2, of the assembly shown in FIG. 5.

FIGS. 5 and 6 show a device similar to that shown in FIGS. 1 to 4, like parts being denoted by like reference numerals. The device shown in FIGS. 5 and 6 differs, from that shown in FIGS. 1 to 4, in that the body 10 is formed with a pair of interior compartments side-by-side, open to the rear of the body, to receive respective elongate, blood-collecting containers of a unit or cartridge 40. The needle 12 of the device communicates, at its inner end, with an internal chamber 41 of the body 10, in which a plunger 42 is disposed, the plunger 42 being formed with a pair of piercing needles 43 for puncturing membranes 44 which close the ends of the blood-collecting containers of the cartridge 40. Typically, the blood-collecting containers will be pre-evacuated.

In use of the device shown in FIGS. 5 and 6, the cartridge 40 is inserted into the body 10 of the device before the device is brought up to the patient. When the tip of the needle 12 of the device is inserted into the patient's blood vessel, blood will pass along the needle and into the chamber 41 at the forward end of the body 10. When the user sees the presence of the blood in this chamber 41 (the wall of body 10 being transparent), the operating knob 24 is retracted slightly: this operating knob is coupled to the plunger 42 to correspondingly retract this plunger and so cause its piercing needles 43 to pierce the membrane 44 at the ends of the blood-collecting containers. The vacuum within these containers causes the blood to be drawn into them, through the needle 12 of the device, its internal chamber 41 and the piercing needles 43 of the plunger 42. The operating knob is arranged so that, upon further retraction, it advances the plunger 16 of the device and so displaces the cannula 30 over the tip of the needle and into the blood vessel, as above-described with reference to FIGS. 1 to 4 of the drawings. In a modification, the operating knob 24 serves only for displacing the plunger 16 and a secondary operating knob is provided, for example alongside or forwardly of the operating knob 24, for retracting the internal plunger 42. Further, the device body 10 may be formed with an internal membrane which closes the chamber 41, the piercing needles 43 of the plunger 42 firstly piercing this membrane and then the membranes 44 of the cartridge 40 when the plunger 42 is retracted.

Figure 7:
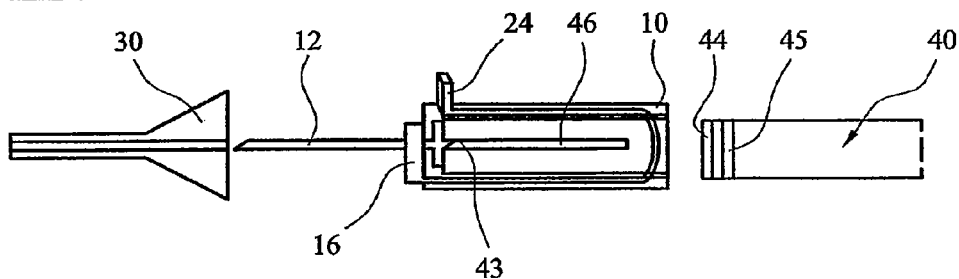
FIG. 7 is a view, similar to FIG. 5, of a third embodiment of device in accordance with the present invention.
Figure 8:
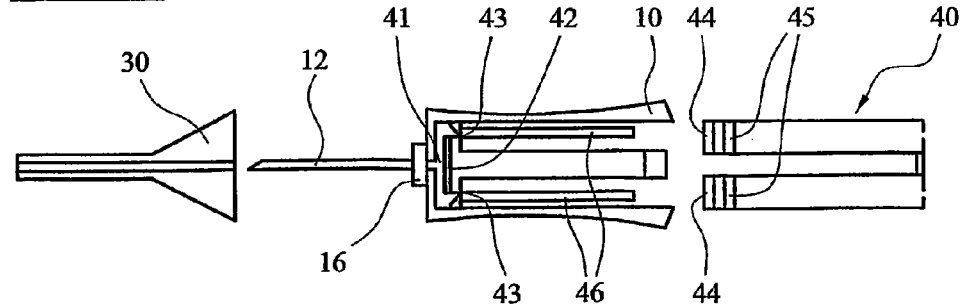
FIG. 8 is a view, similar to FIG. 6, of the assembly shown in FIG. 7.
Figure 9:
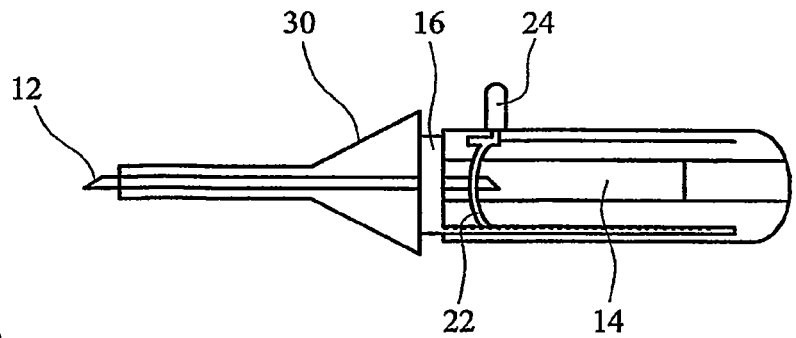
FIG. 9 is a view similar to FIG. 1, showing a modified embodiment of cannula introducing device, in an initial condition ready for use.
Figure 10:
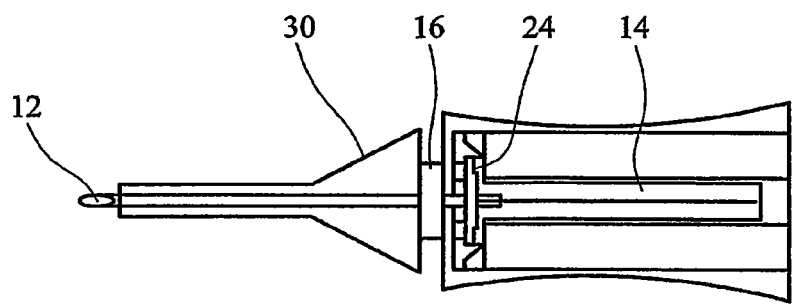
FIG. 10 is a top plan view of the assembly shown in FIG. 9.
Figure 11:
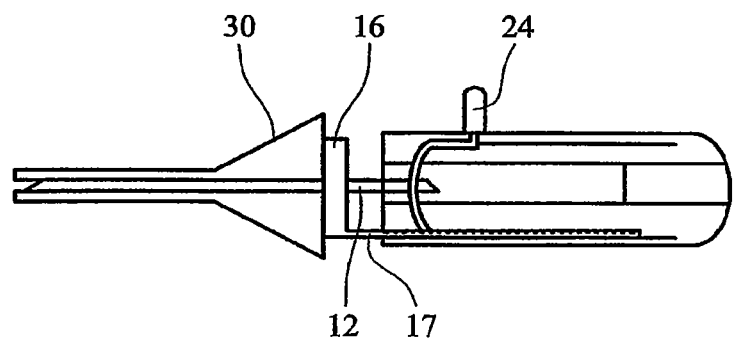
FIG. 11 is a side view of the assembly, corresponding to FIG. 9, showing the plunger of the cannula introducing device advanced through an initial distance, to advance the tip of the cannula over the tip of the needle of the device.
Figure 12:
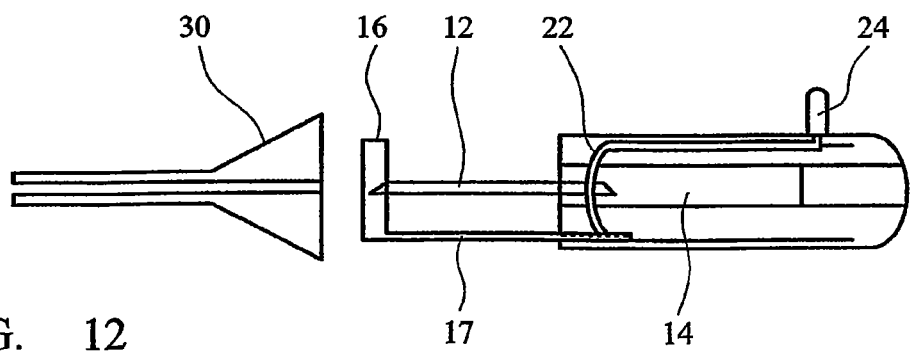
FIG. 12 is a similar view of the assembly, showing the plunger after it has been advanced its full extent.
Figure 13:
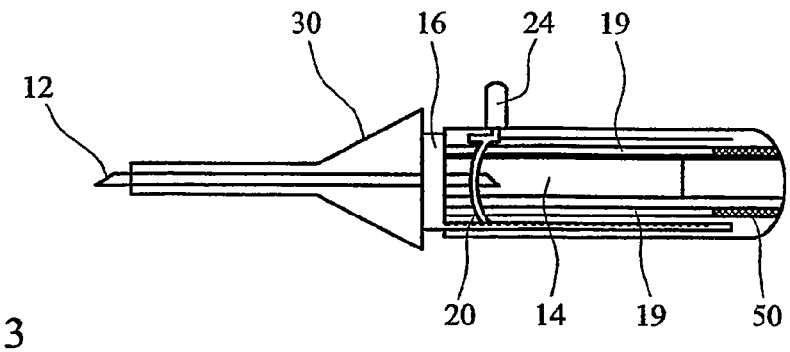
FIG. 13 is a side view, similar to FIG. 1, of a further embodiment of cannula introducing device, shown in an initial condition ready for use.
Figure 14:
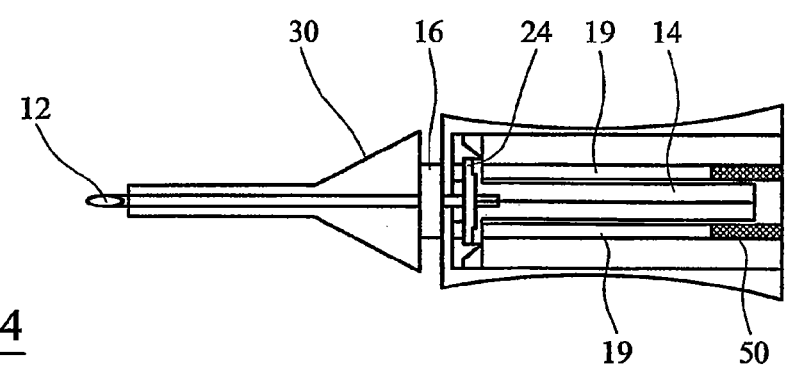
FIG. 14 is a top plan view of the assembly shown in FIG. 13.
Figure 15:
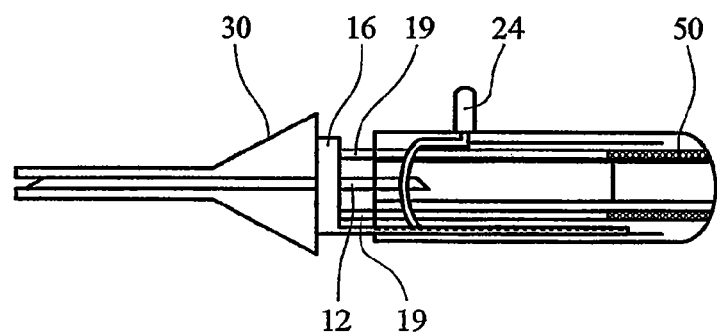
FIG. 15 is a side view of the assembly, corresponding to FIG. 13, showing the plunger of the cannula introducing device advanced through an initial distance, to advance the tip of the cannula over the tip of the needle.

FIGS. 7 and 8 show a similar device to that shown in FIGS. 5 and 6, like parts being denoted by like reference numerals. The device of FIGS. 7 and 8 differs in that it is arranged to create a vacuum in each of the blood-collecting containers of the cartridge 40. Each of these containers is provided with an internal piston 45, initially positioned 25 adjacent the membrane 44 which closes its forward end. The device body 10 is formed internally with a pair of rearwardly directed posts 46 arranged so that, as the cartridge 40 is inserted into the body 10, the posts 46 pierce the membranes 44 of the two containers and abut the pistons 45, and push these pistons rearwardly along the respective containers of the cartridge 40, so creating a vacuum within the containers, forwardly of the pistons 45. It will be appreciated that the rear ends of the containers are formed with openings to allow air to be expelled from the spaces to the rear of the pistons 45: also, the membranes 44 maintain a seal around the posts 46 during the forward movement of the cartridge 40.

FIGS. 9 to 12 show a modification applicable to each of the devices which have been described above. In this device, the elongate flexible element 22 extends from the 5 forward end of the groove or channel in which the operating knob 24 is retained, and round in a curve to a passage extending lengthwise of the body 10 adjacent the side or edge of the body 10, opposite the side in which the groove for the operating knob 24 is formed. The plunger 16 has a rearwards extension 17 to the end of which the element 22 is coupled. Thus, as the operating knob 24 is displaced rearwardly, the element 22 is displaced longitudinally of itself to pull on the extension 17 of the plunger 16 and so pull the plunger forwardly.

Figure 16:
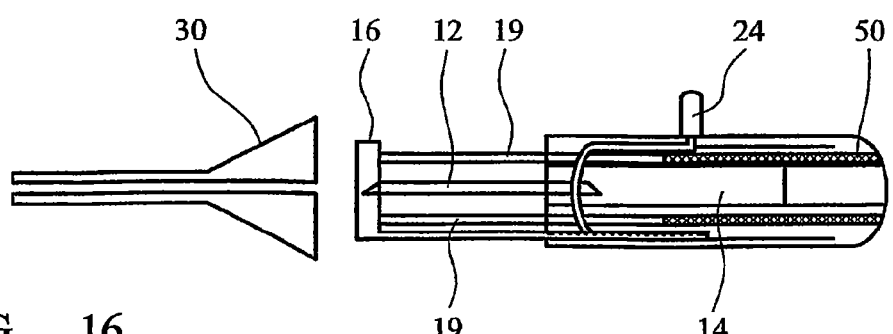
FIG. 16 is a similar side view of the assembly, showing the plunger after it has been advanced to its full extent by a spring of the device.

FIGS. 13 to 16 show a further embodiment which corresponds generally to the embodiment of FIGS. 1 to 4 and incorporating the modification of FIGS. 9 to 12, but also incorporating an additional modification. Thus, retraction of the operating knob 24 serves to pull the plunger 16 forwardly through an initial distance, sufficient to advance the tip of the cannula 30 over the tip of the needle 12 and so introduce the tip of the cannula 30 into the blood vessel (see FIG. 15). The device further includes a compression spring 50, or alternatively a compressed air spring, positioned around the blood collecting chamber 14: at the end of its retracting movement for advancing the plunger 16 over its initial distance as just described, the operating knob 24 serves to actuate or release the spring 50, which then acts on sliding mounting elements 19 of the plunger 16 to advance this fully, until the plunger 16 covers the tip of the needle 12. This final advancement of the plunger 16 is swift and serves to advance the cannula the required distance into the blood vessel, the plunger protecting the tip of the needle 12 (FIG. 16). It will also be noted that the mounting elements 19 of the plunger are elongate in form and extend parallel to the needle 12 and are spaced apart around it, so as to enclose the needle 12 and provide further protection for it, in the extended condition of the plunger.

The invention claimed is:

1. A cannula introducing device comprising:
   an elongate body having a first end portion and a second end portion, a needle projecting from said first end portion, a length extending between said first end portion and said second end portion, and an elongated groove or channel formed along at least a portion of said length;
   an operating member slidably positioned within said groove or channel of said body, said operating member being configured to selectively move along said elongated groove or channel, wherein at least a portion of said operating member projects outwardly from said elongated groove or channel, said operating member being configured to be engaged manually by a user;
   a plunger disposed at said first end portion of said body; and
   an elongate flexible member having a first end attached to said operating member and a second end attached to said plunger, said flexible member extending along said elongated groove or channel between said operating member and said plunger, said elongated groove or channel including a passage having a first portion which extends from a rear end of said elongated groove or channel and curves round to a second portion which extends forwardly to said first end portion of said body, said flexible member being positioned and configured such that movement of said operating member along said elongated groove or channel of said body in a first direction moves said flexible member to push said plunger forwardly along said needle.

2. The device as claimed in claim 1, wherein said plunger is displaceable, by movement of said operating member, far enough to cover the tip of said needle.

3. The device as claimed in claim 1, wherein said plunger is advanced an initial distance by said movement of said operating member, the device further comprising a resilient member configured to advance said plunger through a further distance.

4. The device as claimed in claim 1 wherein said flexible member includes one or more ratchet serrations configured to cooperate with one or more teeth formed on said body to prevent said plunger from being retracted after having been advanced along said needle.

5. The device as claimed in claim 1, wherein said second portion of said passage is disposed in or adjacent a surface of said body remote from or opposite a surface in which said first portion of said passage is formed.

6. The device as claimed in claim 1, wherein said flexible member comprises a guide wire.

7. The device as claimed in claim 6, wherein said guide wire has a flat cross-sectional profile.

8. The device as claimed in claim 1, wherein said body is arranged to receive a fluid-collecting container for receiving blood or other fluid through said needle.

9. The device as claimed in claim 8, wherein said body includes an internal chamber configured to receive blood or other fluid through said needle, said chamber being provided with a second plunger which is configured to be displaced upon displacement of said operating member or of a secondary operating member in said first direction for a piercing needle of said second plunger to pierce a membrane closing the end of said fluid-collecting container.

10. The device as claimed in claim 9, wherein said body is formed with an elongate compartment for the longitudinal insertion of a container of tubular form, said compartment being provided with a longitudinal member for piercing said membrane of said container and to bear on and displace an internal piston of said container as said container is inserted into said compartment.

11. The device as claimed claim 1, further comprising a fluid-collecting container inserted into or for insertion into said body.

12. The device as claimed in claim 1, further comprising a cannula received over said needle.

13. The device of claim 12, wherein said plunger is configured to advance said cannula along said plunger.

14. A cannula introducing device comprising:
   an elongate body arranged to receive a fluid-collecting container for receiving blood or other fluid, said body having:
      a first end portion and a second end portion;
      a needle projecting from said first end portion configured to deliver blood or other fluid to the fluid-collecting container;
      a length extending between said first end portion and said second end portion;
      an elongated groove or channel formed along at least a portion of said length;
   an operating member slidably positioned within said groove or channel of said body, said operating member being configured to selectively move along said elongated groove or channel;
   a plunger disposed at said first end portion of said body; and
   an elongate flexible member having a first end attached to said operating member and a second end attached to said plunger, said flexible member being positioned and configured such that movement of said operating member along said elongated groove or channel of said body in a first direction moves said flexible member to advance said plunger along said needle; and
   wherein said body further includes an internal chamber configured to receive blood or other fluid through said needle, said chamber being provided with a second plunger which is configured to be displaced upon displacement of said operating member or of a secondary operating member in said first direction for a piercing needle of said second plunger to pierce a membrane closing the end of said fluid-collecting container.

15. The device as claimed in claim 14, wherein said body is formed with an elongate compartment for the longitudinal insertion of a container of tubular form, said compartment being provided with a longitudinal member for piercing said membrane of said container and to bear on and displace an internal piston of said container as said container is inserted into said compartment.

16. The device as claimed in claim 14, wherein said flexible member extends along a guideway of said body between said operating member and said plunger.

17. The device as claimed in claim 16, wherein said guideway comprises said elongated groove or channel formed in said body.

18. The device as claimed in claim 14, wherein said flexible member is positioned and configured to push said plunger forwardly along said needle.

19. The device as claimed in claim 14, wherein said flexible member comprises a guide wire.

20. The device as claimed in claim 19, wherein said guide wire has a flat cross-sectional profile.

* * * * *